United States Patent [19]

Biber

[11] Patent Number: 4,794,125
[45] Date of Patent: Dec. 27, 1988

[54] COMPOUNDS HAVING AN IMMUNIZING ACTIVITY

[75] Inventor: Rudolf Biber, Vienna, Austria
[73] Assignee: CL Pharma AG, Linz, Austria
[21] Appl. No.: 186,688
[22] Filed: Apr. 21, 1988

Related U.S. Application Data

[63] Continuation of Ser. No. 862,355, filed as PCT AT85/00019 on Jul. 31, 1985, published as WO 86/00892 on Feb. 13, 1986, abandoned.

[30] Foreign Application Priority Data

Aug. 1, 1984 [AT] Austria .................................. 2468/84

[51] Int. Cl.⁴ .............................................. A61K 31/12
[52] U.S. Cl. ..................................... 514/616; 514/885
[58] Field of Search ....................... 514/885, 613, 616; 260/377

[56] References Cited

FOREIGN PATENT DOCUMENTS 2702137 9/1977 Fed. Rep. of Germany ...... 260/377
351521 7/1979 Netherlands ........................ 514/889

OTHER PUBLICATIONS

Mitarbeit, Handbach de Biologischen Arbeitsmethoden, 1927, pp. 979–980.
Chemical Abstract vol. 87, No. 5728z, Winkelmann 1, 3/10/77, "Substituted 2,6-diaminoanthroquinones".
Chemical Abstract vol 92, No. 116720s, Winkelmann 2, 1979, "Chemotherapeutically Active Anthroquinones".

Primary Examiner—Glennon H. Hollrah
Assistant Examiner—Raymond Covington
Attorney, Agent, or Firm—Wenderoth, Lind & Ponack

[57] ABSTRACT

Process for the preparation of new immunizing compounds of 2,6-di[(monoalkylamino)-acetyl amino]anthraquinone, by reacting 2,6 diaminoanthraquinone with a chloracetic acid chloride and reaction of bis-β-halogenoacylamino anthraquinone thus obtained with methylamine or ethylamine. Also disclosed are compounds thus obtained or acid addition salts thereof, pharmaceutical compositions and utilization of said compounds as immunizing drugs.

3 Claims, No Drawings

COMPOUNDS HAVING AN IMMUNIZING ACTIVITY

This application is a continuation of application Ser. No. 862,355, filed as PCT at 85/00019 on Jul. 31, 1985, published as WO86/00892 on Feb. 13, 1986 now abandoned.

The invention relates to a method for preparing new compounds having an immunizing activity in the series of 2,6-substituted anthraquinones and their physiologically tolerated acid addition salts of the general formula (I)

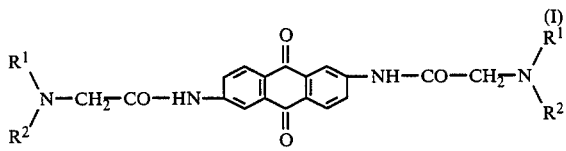

in which $R^1$ and $R^2$ are different, with $R^1$ representing hydrogen and $R^2$ a lower straight-chained alkyl such as methyl or ethyl.

The method for preparing new compounds having an immunizing activity of the general formula (I) and of the acid addition salts thereof consists in the reaction by a per-se known method (e.g., according to the acylation process using chloroacetyl chloride described in "Handbuch der biologischen Arbeitsmethoden" (Handbook of Biological Methods)) by Abderhalden, Part I, Section 2.1, pp. 979ff, 1927) of a 2,6-diaminoanthraquinone of the formula (II)

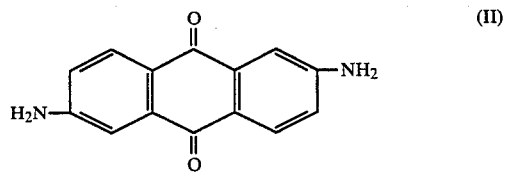

with alpha-chloroacetic acid chloride, and the thusly obtained bis-alpha-haloacylaminoanthraquinone of the formula (III)

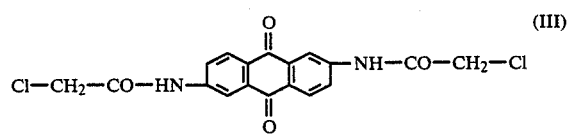

in which $R^1$ and $R^2$ are as defined above, is reacted with a compound of the formula (IV)

in which $R^1$ and $R^2$ are as defined above; the thusly obtained compounds of formula (I) are converted, as required, by addition of a physiologically tolerated acid into the corresponding salt.

According to Austrian Pat. No. 351,521, bis-acetamido anthraquinones, particularly bis-dimethylamino-acetylamino-anthraquinone and bis-hexamethyleneimino-acetylamino-anthraquinone, have antiviral properties. Surprisingly and unexpectedly, it has been demonstrated that compounds of the general formula (I), in which $R^1$ represents hydrogen and $R^2$ methyl or ethyl, have proved to be compounds having a strong immunizing activity.

Biological Efficacy

The compounds prepared in accordance with the invention were investigated using the DTH test (delayed-type hypersensitivity in mice) according to Dietrich, F. M. & Hess, R.: Hypersensitivity in mice. I. Induction of contact sensitivity to oxazolone and inhibition by various chemical compounds. Int. Arch. Allergy 38, 246–259 (1970). The data presented in the table below demonstrate the immunosuppressive efficacy of the new compounds.

Immune suppression produced by 2,6-bis-/(methylamino)acetylamino/-anthraquinone as compared with cyclosporin-A.

| Compound | Dose (mg/kg) | % Inhibition |
|---|---|---|
| 2,6-bis-MAA | 1.0 | 35 |
| CS-A | 70.0 | 35 |

The new compounds (2,6-bis-MAA = 2,6-bis-/(methylamino)-acetylamino/-anthraquinone), CS-A = cyclosporin A, were tested in vivo in OF-1 mice by topical sensitization with antigen (ethanol oxazolone solution). The decrease in the inflammatory response versus untreated animals is expressed as % inhibition. The new compounds exhibit cytostatic activity in vivo and in vitro and are proposed also for treatment of tumors and leukemic disorders in vertebrates. The compounds taught by the invention and their pharmacologically acceptable acid addition salts are active ingredients in pharmaceutical preparations.

The preparations intended for therapeutic purposes inhibit the rejection reaction of homologous transplants in mammals when given in quantities ranging from 0.1 to 50 mg/kg body weight per day. This dosage range can be adjusted to achieve an optimal therapeutic effect as, for example, with the administration of several divided doses: or the dose can also be reduced in accordance with the therapeutic situation. A substantial practical advantage can be seen in the fact that these active ingredients can be administered in any form or manner preferred, e.g., orally, intraperitoneally, subcutaneously, intramuscularly, or intravenously. The active ingredients can be employed alone or in combination with standard pharmaceutical vehicles. Appropriate forms for use include tablets, capsules, suppositories, solutions, syrups, etc.

EXAMPLE 1

2,6-bis-(methylamino)-acetylamino-anthraquinone 3.0 g of 2,6-bis-(chloracetylamino)-anthraquinone were suspended in 150 ml of ethanol in a pressure vessel and were reacted with an excess of an approximately 30% solution of methylamine in ethanol. The mixture was heated to 80° C. for three hours and allowed to return to room temperature overnight. It was concentrated under vacuum and the sediment that precipitated out was drawn off and recrystallized from ethanol. Yield 3.3 g. m.p. 263° C.

The following compound was produced similarly to Example 1:
2,6-bis-/(ethylamino)-acetylamino/-anthraquinone.

I claim:

1. A method for the treatment of a mammal to achieve immunizing activity, which comprises administering to such mammal an immunosuppressive amount of a compound of the formula

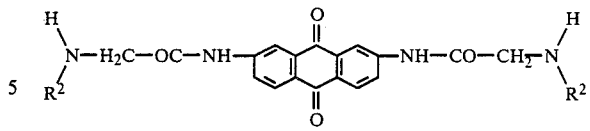

wherein $R^2$ is methyl or ethyl, or an acid addition salt thereof.

2. A method according to claim 1 wherein the compound is 2,6-bis-[(methylamino)-acetylamino]-anthraquinone.

3. A method according to claim 1 wherein the compound is 2,6-bis-[(ethylamino)-acetylamino]-anthraquinone.

* * * * *